US012589102B2

(12) United States Patent
Ugwu et al.

(10) Patent No.: US 12,589,102 B2
(45) Date of Patent: Mar. 31, 2026

(54) INJECTABLE SUSTAINED-RELEASE FORMULATIONS FOR TREATMENT OF JOINT PAIN AND INFLAMMATION

(71) Applicant: FORDOZ Pharma Corp., East Windsor, NJ (US)

(72) Inventors: Sydney Ugwu, North Brunswick, NJ (US); James He, Green Brook, NJ (US); Zengli Fu, Kendall Park, NJ (US)

(73) Assignee: FORDOZ Pharma Corp., East Windsor, NJ (US)

( * ) Notice: Subject to any disclaimer, the term of this patent is extended or adjusted under 35 U.S.C. 154(b) by 1179 days.

(21) Appl. No.: 17/606,023

(22) PCT Filed: May 6, 2020

(86) PCT No.: PCT/US2020/031583
§ 371 (c)(1),
(2) Date: Oct. 23, 2021

(87) PCT Pub. No.: WO2020/227353
PCT Pub. Date: Nov. 12, 2020

(65) Prior Publication Data
US 2022/0096498 A1     Mar. 31, 2022

Related U.S. Application Data

(60) Provisional application No. 62/843,875, filed on May 6, 2019.

(51) Int. Cl.
| | |
|---|---|
| A61K 31/58 | (2006.01) |
| A61K 9/00 | (2006.01) |
| A61K 9/16 | (2006.01) |
| A61K 31/415 | (2006.01) |

(52) U.S. Cl.
CPC ............ *A61K 31/58* (2013.01); *A61K 9/0019* (2013.01); *A61K 9/1641* (2013.01); *A61K 9/1682* (2013.01); *A61K 31/415* (2013.01)

(58) Field of Classification Search
CPC .... A61K 31/58; A61K 9/0019; A61K 9/1641; A61K 9/1682; A61K 31/415; A61K 9/10; A61K 9/5031; A61K 31/573; A61K 31/635; A61K 47/36; A61K 47/38; A61K 45/06; A61P 19/02
See application file for complete search history.

(56) References Cited

U.S. PATENT DOCUMENTS

| | | | |
|---|---|---|---|
| 6,214,387 B1 * | 4/2001 | Berde ................. | A61K 9/1641 424/501 |
| 2014/0154321 A1 * | 6/2014 | Ashton ................. | A61K 31/58 424/484 |
| 2015/0265578 A1 | 9/2015 | McKay | |
| 2018/0092850 A1 | 4/2018 | Anderson et al. | |

FOREIGN PATENT DOCUMENTS

| | | |
|---|---|---|
| WO | 2018104950 | 6/2018 |
| WO | 2020227353 | 11/2020 |

OTHER PUBLICATIONS

Amrite et al., Single Periocular Injection of Celecoxib-PLGA Microparticles Inhibits Diabetes-Induced Elevations in Retinal PGE2, VEGF, and Vascular Leakage. Invest Ophthalmol Vis Sci. Mar. 2006 ; 47(3): 1149-1160 (Year: 2006).*
Dong et al., Intra-articular delivery of liposomal celecoxib-hyaluronate combination for the treatment of osteoarthritis in rabbit model. International Journal of Pharmaceutics 441 (2013) 285-290 (Year: 2013).*
Yang et al., Applicability of a Newly Developed Bioassay for Determining Bioactivity of Anti-Inflammatory Compounds in Release Studies—Celecoxib and Triamcinolone Acetonide Released from Novel PLGA-Based Microspheres. Pharm Res (2015) 32:680-690 (Year: 2015).*
Herrero-Vanrell et al., The potential of using biodegradable microspheres in retinal diseases and other intraocular pathologies. Progress in Retinal and Eye Research 42 (2014) 27-43 (Year: 2014).*
Kumar et al., Sustained efficacy of a single intra-articular dose of FX006 in a rat model of repeated localized knee arthritis. Osteoarthritis and Cartilage 23 (2015) 151-160 (Year: 2015).*
PCT International Search Report, Written Opinion and search strategy for PCT/US2020/031583, Jun. 27, 2019.

* cited by examiner

*Primary Examiner* — Robert A Wax
*Assistant Examiner* — Ngoc-Anh Thi Nguyen
(74) *Attorney, Agent, or Firm* — FLOREK & ENDRES PLLC

(57) ABSTRACT

Drug-loaded microspheres containing both a steroidal anti-inflammatory drug and a non-steroidal anti-inflammatory drug and injectable formulations containing the microspheres for sustained release of both drugs are disclosed. Methods of making such drug-loaded microspheres, formulations, and use of them for treating pains and inflammations, especially those caused by rheumatoid arthritis or osteoarthritis using such microspheres and formulations are also described.

9 Claims, 5 Drawing Sheets

INJECTABLE SUSTAINED-RELEASE FORMULATIONS FOR TREATMENT OF JOINT PAIN AND INFLAMMATION

CROSS-REFERENCE TO RELATED APPLICATION

This application is the U.S. National Stage filing of International Patent Application Number PCT/US2020/031583 filed on May 6, 2020 which claims priority under 35 U.S.C. § 119(e) to U.S. Provisional Application Ser. No. 62/843,875, filed on May 6, 2019, the disclosure of which is incorporated herein by reference in its entirety.

FIELD OF THE INVENTION

The present disclosure relates to sustained-release microsphere formulations for the treatment of joint pain and inflammation, especially rheumatoid arthritis and osteoarthritis.

BACKGROUND OF THE INVENTION

Arthritis is an inflammatory disease that causes joint pain. Generally, there are two main types of arthritis: rheumatoid arthritis (RA) and related diseases, which are immune-mediated systemic inflammatory joint diseases, and osteoarthritis (OA), which is a degenerative joint disease, the onset of which is typically mediated by previous joint injury or other factors. For all of these arthritic conditions, the common symptom is joint and musculoskeletal pain. The inflammation and pain can prevent normal use and function of the joints. Pain and disability from arthritis, joint degeneration, and surgery are generally treated by a combination of oral medications, intramuscular and intra-articular injections of steroidal compounds designed to reduce inflammation.

A distinct benefit of localized anti-inflammatory drug injection is that the relief of inflammation in a particular body area is more rapid and powerful than what can be achieved with traditional anti-inflammatory oral medications. The localized injection also can avoid the systemic side effects that can accompany multiple doses of oral anti-inflammatory medications, notably irritation of the stomach. Furthermore, the hypothalamic-pituitary-adrenal (HPA) axis may be suppressed by the administration of oral corticosteroids, leading to a variety of unwanted side effects.

Accordingly, there is a need for local administration of anti-inflammatories with sustained release for the treatment of pain and inflammation, such as joint pain while reducing the systemic side effects associated with oral administration. In addition, there is a medical need to slow, arrest, reverse or otherwise inhibit structural damage to tissues caused by inflammatory diseases, such as damage to articular tissues resulting from osteoarthritis or rheumatoid arthritis.

SUMMARY OF THE INVENTION

The present invention meets the foregoing needs by providing microspheres loaded with a steroidal anti-inflammatory drug and a non-steroidal anti-inflammatory drug, and injectable formulations comprising the microspheres, which are suspended in a diluent, preferably in the presence of hyaluronic acid.

In one aspect, the present invention provides an injectable sustained-release formulation, comprising:

(a) a steroidal anti-inflammatory drug and a non-steroidal anti-inflammatory drug (NSAID) encapsulated in microspheres of poly(lactic-co-glycolic acid) copolymers (PLGA), wherein the steroidal drug can be initially released from the microspheres in the first week of the administration by injection for immediate pain relief, and then both the steroidal and the non-steroidal drugs are controlled released over several months for sustained pain relief; and (b) a diluent solution in which the drug microspheres are suspended.

The PLGA copolymer can have a molar ratio of lactic acid:glycolic acid between 90:10 and 40:60. The PLGA copolymer can have a molecular weight in the range between 10 kD and 130 kD. The PLGA can also be a blend of PLGA copolymers having different lactic acid:glycolic acid ratios, and/or different average molecular weights, and/or different chain-end groups.

In some embodiments, the corticosteroid anti-inflammatory drug is preferably methylprednisolone acetate (MPA) or triamcinolone acetonide (TCA) and is between 10% and 40% by weight of the microspheres; the NSAID is preferably celecoxib (CXB) and is between 10% to 40% by weight of the microspheres.

Another aspect of the invention is directed to a method of making an injectable sustained-release formulation as described above, comprising the preparation of drug-loaded microspheres by a solid-in-oil-in-water (S/O/W) emulsion process including steps of emulsification, solvent extraction and evaporation, particle washing and particle drying; wherein the organic phase liquid is prepared by dissolving a PLGA copolymer or a blend of PLGA copolymers and a soluble non-steroidal anti-inflammatory drug in a solvent or mixture of solvents followed by suspending micronized solid particles of an insoluble corticosteroid anti-inflammatory drug in the organic phase liquid; and wherein the organic phase liquid is emulsified with a continuous aqueous phase comprising an aqueous solution of polyvinyl alcohol.

A further aspect of the invention is directed to a method of treating pain and/or inflammation, especially rheumatoid arthritis or osteoarthritis, comprising locally injecting a therapeutically effective amount of an injectable sustained-release formulation as disclosed herein into a joint of a patient in need thereof. Such injection is effective to control pain and/or inflammation for at least about three months.

In another aspect, the present invention provides drug-loaded microspheres comprising a steroidal anti-inflammatory drug and a non-steroidal anti-inflammatory drug (NSAID) encapsulated in microspheres of poly(lactic-co-glycolic acid) copolymers (PLGA), wherein the steroidal drug can be initially released from the microspheres in the first week of the administration by injection for immediate pain relief, and then both the steroidal and the non-steroidal drugs are controlled released over several months for sustained pain relief.

In another aspect, the present invention provides a treatment kit comprising a container, a plurality of drug-loaded microspheres in the container, wherein the drug-loaded microspheres are or can be suspended in a diluent solution ready for administration to a subject in need of treatment.

Other aspects or advantages of the present invention will be better appreciated in view of the following detailed description, drawings, examples, and claims.

DETAILED DESCRIPTION OF CERTAIN EMBODIMENTS

Figure 1:
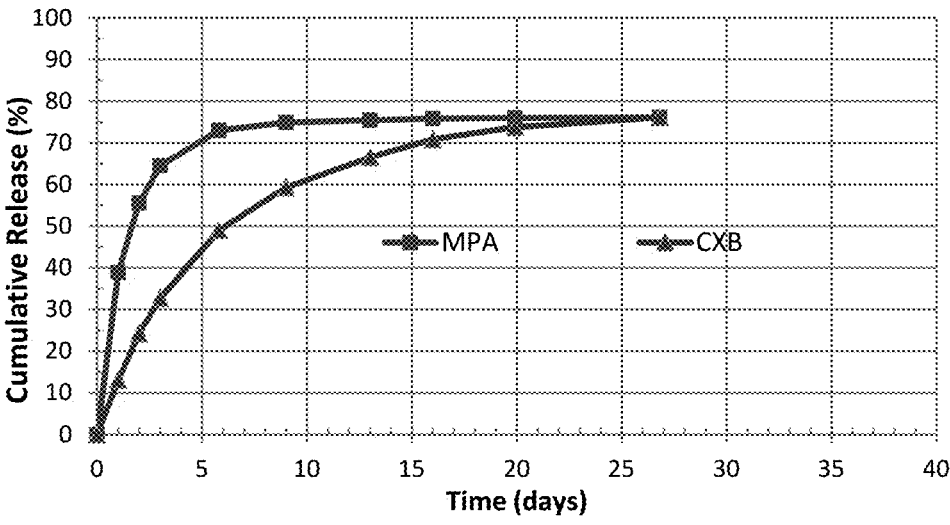
FIG. 1 illustrates the in vitro release profile of methylprednisolone acetate (MPA) and celecoxib (CXB) of Formulation #1 in PBS Buffer w/0.5% SDS, pH 7.4, Shaking Water Bath, 37° C. given in Example 2.

Corticosteroids are medications often used to treat arthritis and related conditions. These medications are widely used because of their overall effectiveness in reducing inflammation, which is the process that causes the joint pain warmth and swelling of arthritis and related conditions. Non-steroidal anti-inflammatory drugs (NSAIDs) are also commonly used to treat rheumatoid arthritis. They help manage the chronic pain, inflammation, and swelling tied to RA.

Hyaluronic acid injections are another treatment option to alleviate osteoarthritis pain. Hyaluronic acid injections in the knee can often produce significant relief for some patients. Furthermore, lab and clinical research suggests that hyaluronic acid may do much more than simply re-lubricate a creaky joint.

It has now been surprisingly discovered that combining these three drugs—corticosteroid, non-steroidal anti-inflammatory drug (NSAID) and hyaluronic acid—in a sustained drug release system with multiple release mechanisms improves the overall management of rheumatoid arthritis and osteoarthritis.

In one aspect, the present invention provides an injectable sustained-release formulation, comprising:

(a) a steroidal anti-inflammatory drug and a non-steroidal anti-inflammatory drug (NSAID) encapsulated in microspheres of poly(lactic-co-glycolic acid) copolymers (PLGA), wherein the steroidal drug can be initially released from the microspheres in the first week of the administration by injection for immediate pain relief, and then both the steroidal and the non-steroidal drugs are controlled released over several months for sustained pain relief; and (b) a diluent solution in which the drug microspheres are suspended.

In some embodiments, the invention provides an injectable sustained-release formulation, comprising: (a) a steroidal anti-inflammatory drug and a non-steroidal anti-inflammatory drug (NSAID), encapsulated in microspheres of poly(lactic-co-glycolic acid) copolymers (PLGA), where the corticosteroid drug has a high initial release rate that gives up to 60% of its total content in the microspheres in the first week of administration, and both the steroidal and the non-steroidal drugs have a sustained controlled release for up to 90 days upon administration by injection; and (b) a diluent solution comprising hyaluronic acid (HA) in which the drug microspheres are suspended.

In some embodiments, the drug-loaded microspheres of the injectable sustained-release formulation preferably have a mean diameter of between 20 μm and 90 μm.

The controlled release of these drugs can be sustained for about one to three months; while the first anti-inflammatory drug is released at a higher initial release rate for an immediate anti-inflammation effect. The hyaluronic acid also acts as a joint lubricant and pain reliever.

In some embodiments, the initial fast release of the corticosteroid drug is cumulatively up to about 30%, up to about 35%, up to about 40%, up to about 45%, up to about 50%, up to about 55%, or up to about 60% of the total in the first week of administration.

In some preferred embodiments, the initial fast release of the corticosteroid drug is cumulatively up to about 50% to about 60% in the first week of administration.

In some embodiments, the controlled release of these drugs can be sustained for about three months with an initial fast release of the first anti-inflammatory drug for an immediate anti-inflammation effect.

In some embodiments, the sustained release is sustained for about one month, or about two months, and sometimes preferably for about three months. The hyaluronic acid also acts as a joint lubricant and pain reliever during this time.

In some embodiments, the steroidal drug is selected from the group consisting of cortisone, betamethasone, betamethasone acetate, betamethasone dipropionate, betamethasone valerate, cortivasol, dexamethasone, dexamethasone acetate, dexamethasone sodium phosphate, hydrocortisone acetate, hydrocortisone sodium phosphate, hydrocortisone sodium succinate, hydrocortisone valerate, hydrocortisone aceponate, hydrocortisone butyrate, hydrocortisone cypionate, hydrocortisone proputate, methylprednisolone, methylprednisolone aceponate, methylprednisolone acetate, methylprednisolone sodium phosphate, methylprednisolone sodium succinate, prednisolone, prednisolone acetate, prednisolone, metasulfobenzoate, prednisolone sodium phosphate, prednisolone, steaglate, prednisolone tebutate, triamcinolone, triamcinolone acetonide, triamcinolone acetonide 21-palmitate, triamcinolone benetonide, triamcinolone diacetate, triamcinolone hexacetonide, alclometasone, alclometasone dipropionate, amcinonide, amelometasone, beclomethasone, beclomethasone dipropionate, monohydrate, budesonide, butixocort, butixocort propionate, ciclesonide, ciprocinonide, clobestasol, clobestasol propionate, clocortolone, clobestasone, clobestasone butyrate, clocortolone pivalate, cloprednol, cortisone, cortisone acetate, deflazacort, domorednate, deprodone, deprodone propionate, desonide, desoximethasone, desoxycotone, desoxycortone acetate, dichlorisone, diflorasone diflorasone diacetate, diflucortolone, difluprdnate, fluclorolone, fluclorolone acetonide, fludrocortisone flucortisone acetate fludroxycortide, flumethasone, flumethasone pivalate, flunisolide, fluocinolone, fluocinolone acetonide, flucortin, flucortolone, fluorometholone, fluticasone, fluticasone furoate, fluticasone propionate, fluorometholone acetate, fluoxymesterone, fluperolone, fluprednidene, fluprednidene acetate, fluprednisolone, formocortal, halcinonide, halobetasol propionate, halometasone, halopredone, halopredone acetate, hydrocortamate, isoflupredone, isoflupredone, acetate, itrocinonide, loteprednol etabonate, mazipredone, meclorisone, meclorisone dibutyrate, medrysone, meprednisone, mometasone, mometasone furoate, mometasone furoate monohydrate, nivacortol, paramethasone, paramethasone acetate, prednazoline, prednicarbate, prednisolone, prednylidene, procinonide, rofileponide, rimexoone, timobesone, tipredane, tixocortol, toxocortol pivalate, and tralonidel, or the like, and stereoisomers thereof, including racemates or enantiomers.

In some embodiments, the NSAID is selected from the group consisting of celecoxib (CXB), mefenamic acid, tolfenamic acid, flufenamic acid diclofenac, sulindac, fenbufen, indomethacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tometin, diflunisal, floctafenine, and tinoridine, or the like, and stereoisomers thereof, including racemates or enantiomers.

In some embodiments, the corticosteroid anti-inflammatory drug is advantageously selected from the group consisting of methylprednisolone acetate (MPA), triamcinolone acetonide (TCA), dexamethasone, hydrocortisone, prednisolone, and prednisone, or the like, and combinations thereof.

In some embodiments, the NSAID is advantageously selected from the group consisting of celecoxib (CXB), diclofenac, indomethacin, ibuprofen, naproxen, meloxicam, mefenamic acid, and oxaprozin, or the like, and combinations thereof.

In some embodiments, the PLGA copolymer has a monomer unit molar ratio of lactic acid:glycolic acid (L/G ratio) between about 90:10 and about 40:60.

In some embodiments, the L/G molar ratio of the PLGA copolymer is between about 80:20 and about 40:60, or about 70:30 and about 40:60, or about 60:40 and about 40:60, or about 50:50 and about 40:60.

In some preferred embodiments, the L/G molar ratio of the PLGA copolymer is about 50:50, about 75:25, or between about 50:50 and about 75:25.

In some embodiments, the PLGA copolymer has a molecular weight in the range between about 10 kD and about 130 kD.

In some embodiments, the PLGA copolymer has a molecular weight in the range of about 10 to about 125 kD, or about 20 to about 120 kD, or about 30 to about 110 kD, or about 40 to about 100 kD, or about 50 to about 90 kD, or about 60 to about 80 kD, or any combinations thereof, such as about 10 to about 50 KD, about 20 to about 40 KD, about 40 to about 60 KD, about 50 to about 70 KD, or the like.

In some embodiments, the PLGA copolymer is a mixture of PLGA copolymers having different lactic acid:glycolic acid ratios, and/or different average molecular weights, and/or different chain-end groups.

Suitable chain-end groups include, but are not limited to, free acid- (i.e., carboxyl) and ester-end groups.

In some embodiments, sometimes preferably, the corticosteroid anti-inflammatory drug is MPA or TCA, or a combination thereof.

In some embodiments, the corticosteroid anti-inflammatory drug, such as MPA, TCA, or a combination thereof, is between about 10% and about 40%, or about 15% to about 35%, or about 20% to about 30% by weight of the microspheres.

In some embodiments, the corticosteroid anti-inflammatory drug, such as MPA, TCA, or a combination thereof, is about 10%, or about 15%, or about 20%, or about 25%, or about 30%, or about 35%, or about 40% by weight of the microspheres.

In some embodiments, sometimes preferably, the NSAID is preferably CXB, or the like.

In some embodiments, the NSAID, such as CXB or the like, is between about 10% and about 40%, or about 15% to about 35%, or about 20% to about 30% by weight of the microspheres.

In some embodiments, sometimes preferably, the NSAID, such as CXB or the like, is about 10%, or about 15%, or about 20%, or about 25%, or about 30%, or about 35%, or about 40% by weight of the microspheres.

In some embodiments, sometimes preferably, the drug-loaded microspheres of the injectable sustained-release formulation have a mean diameter between about 20 μm and about 90 μm, preferably about 25 to about 85 μm, or about 30 to about 80 μm, or about 35 to about 75 μm, about 40 to about 70 μm, or about 45 to about 65 μm, or about 50 to about 60 μm.

Another aspect of the invention is directed to a method of making an injectable sustained-release formulation as described above, comprising the steps of preparing drug-loaded microspheres by a solid-in-oil-in-water (S/O/W) emulsion process including emulsification, solvent extraction and evaporation, particle washing and particle drying; wherein the organic phase liquid is prepared by dissolving a PLGA copolymer or a blend of PLGA copolymers and a soluble non-steroidal anti-inflammatory drug in a solvent or mixture of solvents selected from the group consisting of dichloromethane, ethyl acetate, benzyl alcohol, methanol, ethanol, isopropyl alcohol, 1-butanol, iso-butyl alcohol, 1-pentanol, isopentyl alcohol, and 1-hexanol, followed by suspending micronized solid particles of an insoluble corticosteroid anti-inflammatory drug in the organic phase liquid; and wherein the said organic phase liquid is emulsified with a continuous aqueous phase comprising an aqueous solution of polyvinyl alcohol, gelatins, polysorbate 20, polysorbate 80, and other surfactants and dispersing agents.

In one embodiment, the method of making an injectable sustained-release formulation as described above, comprises a step of preparing the drug-loaded microspheres by an oil-in-water (0/W) emulsification process, where a dispersed organic phase comprising a PLGA copolymer mixed with a steroidal drug and a non-steroidal drug in a suitable solvent or solvent mixture is emulsified with a continuous aqueous phase comprising an aqueous polyvinyl alcohol (PVA) solution.

In some embodiments, sometimes preferably, the aqueous phase comprises about 1% PVA in water.

In some embodiments, sometimes preferably, the solvent is selected from the group consisting of dichloromethane (DCM), ethyl acetate (EtOAc), benzyl alcohol (BA), methanol, ethanol, isopropyl alcohol (IPA), 1-butanol, iso-butyl alcohol, 1-pentanol, isopentyl alcohol, 1-hexanol, and mixtures of two or more thereof.

In some embodiments, sometimes preferably, the organic solvent is DCM or a mixture of DCM and EtOAc. In some embodiments, the ratio of DCM and EtOAc is between about 10:0 and about 3:7 by volume.

In another aspect, the present invention provides a drug-loaded microsphere comprising a steroidal anti-inflammatory drug and a non-steroidal anti-inflammatory drug (NSAID), encapsulated in the microsphere of poly(lactic-co-glycolic acid) copolymers (PLGA), in any embodiments described herein. The drug-loaded microspheres can be suspended in a diluent solution ready for administration to a subject having pain or inflammation in need of treatment.

In some embodiments, sometimes preferably, once administered to a subject in a suitable formulation, the steroidal drug in the microsphere has a high initial release rate that gives up to 60% of its total content in the microsphere in the first week of administration and both the steroidal and the non-steroidal drugs have a sustained controlled release for up to about 90 days upon administration by injection.

In another aspect, the present invention provides drug-loaded microspheres comprising a steroidal anti-inflammatory drug and a non-steroidal anti-inflammatory drug (NSAID) encapsulated in microspheres of poly(lactic-co-glycolic acid) copolymers (PLGA), wherein the steroidal drug can be initially released from the microspheres in the first week of the administration by injection for immediate pain relief, and then both the steroidal and the non-steroidal drugs are controlled released over several months for sustained pain relief.

In another aspect, the present invention provides use of a drug-loaded microsphere as disclosed herein in any embodiments in the manufacture of a medicament for treatment of pain and/or inflammation, preferably caused by arthritis, wherein the arthritis is optionally, and sometimes preferably, rheumatoid arthritis or osteoarthritis.

In another aspect, the present invention provides a treatment kit comprising a container, a plurality of drug-loaded microspheres in the container, wherein the drug-loaded microspheres are or can be suspended in a diluent solution ready for administration to a subject having arthritis in need of treatment.

In any embodiments of any aspects disclosed herein, suitable steroidal drugs for the drug-loaded microspheres include, but are not limited to, cortisone, betamethasone, betamethasone acetate, betamethasone dipropionate, betamethasone valerate, cortivasol, dexamethasone, dexamethasone acetate, dexamethasone sodium phosphate, hydrocortisone acetate, hydrocortisone sodium phosphate, hydrocortisone sodium succinate, hydrocortisone valerate, hydrocortisone aceponate, hydrocortisone butyrate, hydrocortisone cypionate, hydrocortisone proputate, methylprednisolone, methylprednisolone aceponate, methylprednisolone acetate, methylprednisolone sodium phosphate, methylprednisolone sodium succinate, prednisolone, prednisolone acetate, prednisolone, metasulfobenzoate, prednisolone sodium phosphate, prednisolone, steaglate, prednisolone tebutate, triamcinolone, triamcinolone acetonide, triamcinolone acetonide 21-palmitate, triamcinolone benetonide, triamcinolone diacetate, triamcinolone hexacetonide, alclometasone, alclometasone dipropionate, amcinonide, amelometasone, beclomethasone, beclomethasone dipropionate, monohydrate, budesonide, butixocort, butixocort propionate, ciclesonide, ciprocinonide, clobestasol, clobestasol propionate, clocortolone, clobestasone, clobestasone butyrate, clocortolone pivalate, cloprednol, cortisone, cortisone acetate, deflazacort, domorednate, deprodone, deprodone propionate, desonide, desoximethasone, desoxycotone, desoxycortone acetate, dichlorisone, diflorasone diflorasone diacetate, diflucortolone, difluprdnate, fluclorolone, fluclorolone acetonide, fludrocortisone flucortisone acetate fludroxycortide, flumethasone, flumethasone pivalate, flunisolide, fluocinolone, fluocinolone acetonide, flucortin, flucortolone, fluorometholone, fluticasone, fluticasone furoate, fluticasone propionate, fluorometholone acetate, fluoxymesterone, fluperolone, fluprednidene, fluprednidene acetate, fluprednisolone, formocortal, halcinonide, halobetasol propionate, halometasone, halopredone, halopredone acetate, hydrocortamate, isoflupredone, isoflupredone, acetate, itrocinonide, loteprednol etabonate, mazipredone, meclorisone, meclorisone dibutyrate, medrysone, meprednisone, mometasone, mometasone furoate, mometasone furoate monohydrate, nivacortol, paramethasone, paramethasone acetate, prednazoline, prednicarbate, prednisolone, prednylidene, procinonide, rofileponide, rimexoone, timobesone, tipredane, tixocortol, toxocortol pivalate, and tralonidel, or the like, including their stereoisomers, racemates, or enantiomers.

In any embodiments of any aspects disclosed herein, suitable NSAIDs be used for the drug-loaded microspheres include, but are not limited to, is selected from the group consisting of celecoxib (CXB), mefenamic acid, tolfenamic acid, flufenamic acid diclofenac, sulindac, fenbufen, indomethacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tometin, diflunisal, floctafenine, tinoridine and as racemers or enantiomers, or the like, including their stereoisomers, racemates, or enantiomers.

As a person skilled in the art would understand, in any aspects disclosed herein, the present invention encompasses any embodiments disclosed herein, including any reasonable combinations of different components and/or parameters.

The diluent solution can be any type of diluent solution suitable for suspending drug-loaded microspheres ready for administration, which is typically made and stored under sterile conditions. In some embodiments, sometimes preferred, the diluent solution contains hyaluronic acid or the like as joint lubricant and/or pain reliever.

The following are examples of suspending diluent formulations containing hyaluronic acid (HA) for the dispersion of drug-loaded microspheres of the invention:

Diluent Formulation 1:

| Ingredient | Concentration |
|---|---|
| HA | 1.0% by weight |
| Polysorbate 80 | 0.05% by weight |
| Disodium hydrogen phosphate dihydrate, 5-10 mM | 98.9% |
| pH | 6-7 |

Diluent Formulation 2:

| Ingredient | Concentration |
|---|---|
| HA | 1.0% by weight |
| Polysorbate 80 | 0.04% by weight |
| Citric Acid, 10-20 mM | 98.9% |
| pH | 6-7 |

Diluent Formulation 3:

| Ingredient | Concentration |
|---|---|
| HA | 1.0% by weight |
| Carboxymethylcellulose Sodium | 0.5% weight |

-continued

| Ingredient | Concentration |
|---|---|
| Polysorbate 80 | 0.04% weight |
| Disodium hydrogen phosphate dihydrate, 5-10 mM | 98.5% |
| pH | 6-7 |

Diluent Formulation 4:

| Ingredient | Concentration |
|---|---|
| HA | 1.0% by weight |
| Carboxymethylcellulose Sodium | 0.5% weight |
| Polysorbate 80 | 0.04% weight |
| Citric Acid | 98.5% |
| pH | 6-7 |

A further aspect of the invention is directed to a method of treating rheumatoid arthritis or osteoarthritis, comprising locally injecting a therapeutically effective amount of the above-described injectable sustained-release formulation, into a joint of a patient in need thereof. Preferably said patient is a human. Such injection is effective to control pain and/or inflammation for at least about one month or about two months, preferably for at least about three months. Some preferred injection routes of compositions described herein include: intra-articular, intramuscular, and intraspinal.

This invention can be also applied to other drug products such as oral suspensions. For example, the TCA/CXB loaded microspheres powder can be suspended in appropriate vehicles and administered oral suspensions to patients who cannot take oral tablets or capsules. The TCA/CXB microspheres powder can also be encapsulated in capsules or formulated as tablets for oral administration. TCA/CXB loaded microsphere capsules or tablets formulated this way will release the drug in a sustained release fashion and reduce the frequency of administration compared to conventional tablets and capsules.

In another aspect of the invention, the present invention provides a combination of a device or kit containing a pharmaceutical composition disclosed here for convenience of administration, for example, a syringe containing a single dose of microspheres containing a steroidal anti-inflammatory drug and a non-steroidal anti-inflammatory drug for treating a condition that is treatable by the sustained release form of microspheres. Such a syringe can optionally be attached to a needle ready for injection. Such a needle should have a bore size that is appropriate for introduction of the microspheres, and may be optionally capped with a needle cover. All such device or kit should be in sterile conditions and preferably stored and readily transportable under such conditions.

The formulations of microspheres of the present invention can be prepared to have qualities suitable to be delivered by other parenteral and non-parenteral routes such as oral, buccal, intrathecal, nasal, pulmonary, transdermal, transmucosal and the like.

In other aspects, the formulation of microspheres can be administered alone, or in appropriate combination with other active agents or drug therapies, as part of a pharmaceutical formulation. Such a pharmaceutical formulation may include the microspheres in combination with any standard physiologically and/or pharmaceutically acceptable carriers which are known in the art. The formulation compositions preferably are sterile and contain a therapeutically effective amount of the microsphere in a unit of weight or volume suitable for administration to a patient.

Unless specifically defined, any terms used in this application take ordinary meanings as would be understood by those of skill in the art.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10%, sometimes preferably 5%, and sometimes preferably 2%, of the indicated number. For example, "about 10%" may indicate a range of 9% to 11%, sometimes preferably 9.5% to 10.5%; and "about 20" may mean from 18 to 22, and sometimes preferably 19 to 21. Other meanings of "about" may be apparent from the context, such as rounding off, so, for example "about 1" may also mean from 0.5 to 1.4. Similarly, "about 0.2" may encompass the value 0.22.

As used herein, the singular forms "a," "an," and "the" include plural reference, and vice versa, any plural forms include singular reference, unless the context clearly dictates otherwise.

The terms "comprising," "having," "including," and "containing," or the like, are to be construed as open-ended terms (i.e., meaning "including, but not limited to,") unless otherwise noted.

As used herein, the term "microspheres" or the like, refers to small spherical or substantially spherical particles with diameters in the range of about 1 μm to about 1000 μm, for example, in some embodiments, about 10 μm to about 500 μm, in some embodiments, about 20 μm to about 150 μm, and in some embodiments, more specifically, from about 50 μm to about 100 μm, produced from natural and synthetic polymers, which can encapsulate a variety of drugs.

The term "sustained release," or the like, refers to a drug delivery system, such as microspheres, that releases the desired amount of drug molecule (or active pharmaceutical ingredient, API) for a defined or extended period of time ranging from days to months, for example, in some embodiments, release of about 80 to 90% of drug molecule in 5 to 15 days, and in some embodiments, release of about 30% of drug molecule in about 30 days, etc. The release of the drug molecule from the microspheres of the invention can take in a continuous, discontinuous, linear or nonlinear manner, preferably continuous and linear manner.

The term "controlled release," or the like, refers to a delivery system, such as microspheres, that facilitates the release of pre-determined amount of drug in a controlled-rate fashion. In the present invention, the terms "sustained release" and "controlled" are sometimes used interchangeably.

The term "substantially," as used herein, means "for the most part" or "essentially", as would be understood by a person of ordinary skill in the art.

The term "pharmaceutically acceptable" describes a material that is not biologically or otherwise undesirable, i.e. without causing an unacceptable level of undesirable biological effects or interacting in a deleterious manner.

The term "therapeutically effective amount" means an amount effective to deliver a therapeutically effective amount of an amount of active agent needed to delay the onset of, inhibit the progression of, or halt altogether the particular disease, disorder or condition being treated, or to otherwise provide the desired effect on the subject to be treated. As one of ordinary skill in the art would understand, a therapeutically effective amount varies with the patient's age, condition, and gender, as well as the nature and extent of the disease, disorder or condition in the patient, and the dosage may be adjusted by the individual physician (or veterinarian).

The terms "treating" and "treatment" refer to reversing, alleviating, inhibiting, or slowing the progress of the disease, disorder, or condition to which such terms apply, or one or more symptoms of such disease, disorder, or condition.

The term "subject" or "patient" used herein refers to a human patient or a mammalian animal, such as cat, dog, cow, horse, monkey, or the like.

The following non-limiting examples will further illustrate certain aspects of the present invention.

EXAMPLES

Example 1. List of Drug Substances and PLGA Raw Materials Used in Formulations 1-8

A. Drug Substances
1) MPA: Methylprednisolone Acetate, Micronized powder, U.S.P., Spectrum Chemical MFG Corp.
2) TCA: Triamcinolone Acetonide (9α-Fluoro-11β,21-dihydroxy-16α,17α-isopropylidenedioxypregna-1,4-diene,3,20-dione), Micronized powder, U.S.P., Spectrum Chemical MFG Corp.
3) CXB: Celecoxib (5-(4-Methylphenyl)-1-(4-sulfamoylphenyl)-3-(trifluoromethyl)pyrazole), Powder crystals, TCI America.
B. PLGA polymers with different lactide/glycolide ratio, molecular weight, and chain-end groups are listed in Table 1.

TABLE 1

List of the PLGA polymers used in preparing Formulations 1-8.

| PLGA Polymer | L/G Ratio | Mw/IV* | End Group | Source |
|---|---|---|---|---|
| Resomer ® RG 505 | 50:50 | 54-69 kD/IV = 0.61~0.74 dL/g | Ester | Sigma Aldrich/ Evonik |
| Resomer ® RG 503H | 50:50 | 24-38 kD/IV = 0.32~0.44 dL/g | Carboxyl | Sigma Aldrich/ Evonik |
| LACTEL ® B6007-1P | 75:25 | IV = 0.55~0.75 dL/g | Ester | Durect Corporation |
| LACTEL ® B6012-4P | 75:25 | IV = 0.70~0.90 dL/g | Carboxyl | Durect Corporation |

*25° C., 0.1% in chloroform

Example 2. Preparation of Methylprednisolone Acetate (MPA) and Celecoxib (CXB) Loaded PLGA Microsphere Formulations (Formulations 1 and 2)

The formulations were prepared by a solid-in-oil-in-water (S/O/W) emulsion method. The drug-loaded microspheres were formed by a process comprising an emulsification step followed by solvent extraction/evaporation, washing and drying steps. First, an organic phase was prepared by dissolving 450 mg of one or a mixture of the PLGA polymers listed in Table 1 and 150 mg of CXB (see Example 1) in 3.0 mL of dichloromethane (DCM) or 3.0 mL of 1:1 mixture of DCM and ethyl acetate (EtOAc). Once a clear solution was formed, 150 mg of micronized MPA powder (see Example 1) was added into the solution and intensive stirring was used to uniformly disperse the MPA particles. Subsequently, the organic phase liquid was injected into 40 mL of a water solution of 1% PVA (Polyvinyl alcohol 8-88, EMPROVE® exp Ph Eur, USP, JPE) and the solution is immediately emulsified with a Polytron PT-3100 homogenizer running at a mixing speed of about 800 to 1000 rpm. After a total mixing time of about 1.5 minute, the emulsion was immediately transferred into 300 mL of water in a larger container. The emulsion was stirred at medium speed for about 4 hours to remove the solvent. The final suspension of solidified microspheres was sieved through a 150-μm screen to separate any large agglomerates, and the product was de-watered and collected on a 25-μm screen. The microspheres were further washed with deionized water and dried in 2-8° C. air for overnight, followed by drying in vacuum (below 0.5 Torr) for 6 hours.

Table 2 provides some detailed information of Formulations 1 and 2, including the compositions of the raw materials and the measured drug loading and particle size distribution of the formulations, where for the particle size distribution, D10, D50, and D90 represent the particle sizes under which the volume percentages are 10%, 50%, and 90%, respectively, and the Span value is calculated by (D90-D10)/D50.

TABLE 2

Detailed Information of MPA/CXB Loaded Microsphere Formulations #1 and #2

| Formulation | Organic Phase | % Drug Loading | | Particle Size Distribution | | | |
|---|---|---|---|---|---|---|---|
| # | Composition | MPA | CXB | D10 | D50 | D90 | Span |
| 1 | Resomer ® RG 505: 450 mg MPA: 150 mg CXB: 150 mg Dichloromethane: 3.0 mL | 18.5% | 17.8% | 37.2 μm | 59.7 μm | 91.5 μm | 0.908 |
| 2 | Resomer ® RG 505: 450 mg MPA: 150 mg CXB: 150 mg Dichloromethane/ ethyl acetate (1:1): 3.0 mL | 18.7% | 18.7% | 40.0 μm | 64.9 μm | 101.8 μm | 0.953 |

Figure 2:
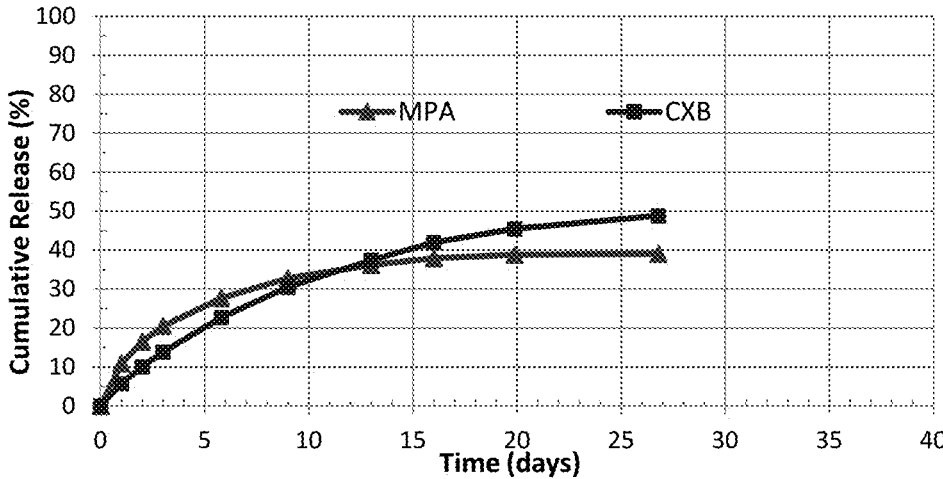
FIG. 2 illustrates the in vitro release profile of methyl-prednisolone acetate and celecoxib of Formulation #2 in PBS Buffer w/0.5% SDS, pH 7.4, Shaking Water Bath, 37° C. given in Example 2.
Figure 3:
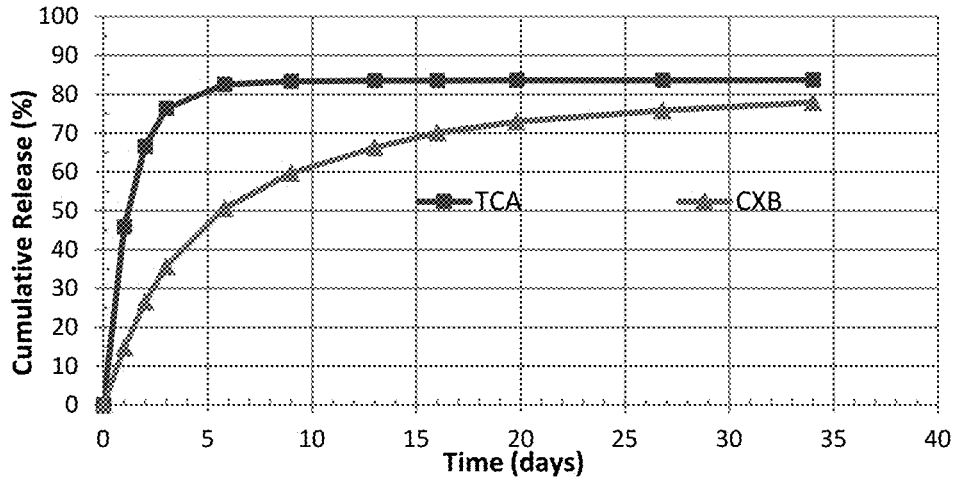
FIG. 3 illustrates the in vitro release profile of triamcinolone acetonide (TCA) and celecoxib (CXB) of Formulation #3 in PBS Buffer w/0.5% SDS, pH 7.4, Shaking Water Bath, 37° C. given in Example 3.

The in vitro cumulative release profiles of MPA and CXB of Formulations #1 and #2 are shown in FIG. 1 and FIG. 2. Both formulations use a medium-to-high molecular weight, ester end-capped PLGA with L/G ratio of 50:50 (Resmer® RG505). Using dichloromethane as the solvent for the dispersed organic phase, Formulation #1 gives a fast initial release rate for MPA, while the release of CXB is relatively slower (FIG. 1). However, in Formulation #2, when using a mixture of dichloromethane and ethyl acetate (1:1) as the solvent for the dispersed organic phase, the release rate of both MPA and CXB are much slower and the release of both drugs can be sustained for a much longer time (FIG. 2).

Example 3. Preparation of Triamcinolone Acetonide (TCA) and Celecoxib (CXB) Loaded PLGA Microsphere Formulations (Formulations 3 to 8)

The formulations were prepared by a solid-in-oil-in-water (S/O/W) emulsion method. The drug-loaded microspheres were formed by a process comprising an emulsification step followed by solvent extraction/evaporation, washing and drying steps. First, an organic phase was prepared by dissolving 450 mg of one or a mixture of the PLGA polymers listed in Table 1 and 150 mg of CXB (see Example 1) in 3.0 mL of dichloromethane (DCM) or 3.0 mL of 1:1 mixture of DCM and ethyl acetate (EtOAc). Once a clear solution was formed, 150 mg of micronized TCA powder (see Example 1) was added into the solution and intensive stirring was used to uniformly disperse the TCA particles. Subsequently, the organic phase liquid was injected into 40 mL of water solution of 1% PVA (Polyvinyl alcohol 8-88, EMPROVE® exp Ph Eur, USP, JPE) and the solution is immediately emulsified with a Polytron PT-3100 homogenizer running at a mixing speed of about 800 to 1000 rpm. After a total mixing time of about 1.5 minute, the emulsion was immediately transferred into 300 mL of water in a larger container. The emulsion was stirred at medium speed for about 4 hours to remove the solvent. The final suspension of solidified microspheres was sieved through a 150-μm screen to separate any large agglomerates, and the product was de-watered and collected on a 25-μm screen. The microspheres were further washed with deionized water and dried in 2-8° C. air for overnight, followed by drying in vacuum (below 0.5 Torr) for 6 hours.

Table 3 provides some detailed information of Formulations 3 to 8, including the compositions of the raw materials and the measured drug loading and particle size distribution of the formulations, where for the particle size distribution, D10, D50, and D90 represent the particle sizes under which the volume percentages are 10%, 50%, and 90%, respectively, and the Span value is calculated by (D90-D10)/D50.

TABLE 3

Detailed Information of TCA/CXB Loaded Microsphere Formulations, #3 to #8

| Formulation | Organic Phase | % Drug Loading | | Particle Size Distribution | | | |
|---|---|---|---|---|---|---|---|
| # | Composition | TCA | CXB | D10 | D50 | D90 | Span |
| 3 | Resomer ® RG 505: 450 mg TCA: 150 mg CXB: 150 mg Dichloromethane: 3.0 mL | 19.2% | 18.7% | 32.9 μm | 48.3 μm | 71.1 μm | 0.791 |
| 4 | Resomer ® RG 505: 450 mg TCA: 150 mg CXB: 150 mg DCM/EtOAc (1:1): 3.0 mL | 18.7% | 18.7% | 43.4 μm | 76.1 μm | 132.0 μm | 1.163 |
| 5 | LACTEL ® B6012- 4P: 450 mg TCA: 150 mg | 18.9% | 18.5% | 42.9 μm | 69.2 μm | 110.6 μm | 0.979 |

TABLE 3-continued

Detailed Information of TCA/CXB Loaded Microsphere Formulations, #3 to #8

| Formulation | Organic Phase | % Drug Loading | | Particle Size Distribution | | | |
|---|---|---|---|---|---|---|---|
| # | Composition | TCA | CXB | D10 | D50 | D90 | Span |
| 6 | CXB: 150 mg Dichloromethane: 3.0 mL LACTEL ® B6012- 4P: 450 mg TCA: 150 mg CXB: 150 mg | 18.7% | 18.3% | 47.0 µm | 81.1 µm | 139.9 µm | 1.144 |
| 7 | DCM/EtOAc (1:1): 3.0 mL LACTEL ® B6007- 1P: 450 mg TCA: 150 mg CXB: 150 mg Dichloromethane: 3.0 mL | 19.2% | 19.6% | 30.0 µm | 43.9 µm | 64.7 µm | 0.790 |
| 8 | Resomer ® RG 505: 100 mg Resomer ® RG 503H: 350 mg TCA: 150 mg CXB: 150 mg Dichloromethane/ ethyl acetate (1:1): 3.0 mL | 17.7% | 17.5% | 31.9 µm | 48.9 µm | 74.2 µm | 0.865 |

The in vitro cumulative release profiles of TCA and CXB of Formulations #3 to #8 are shown in FIG. 3 to FIG. 8.

Figure 4:
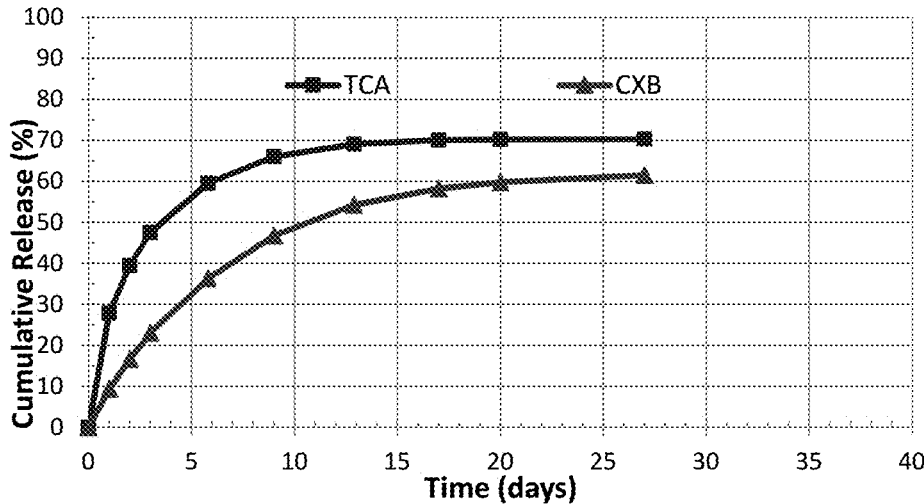
FIG. 4 illustrates the in vitro release profile triamcinolone acetonide and celecoxib of Formulation #4 in PBS Buffer w/0.5% SDS, pH 7.4, Shaking Water Bath, 37° C. given in Example 3.
Figure 5:
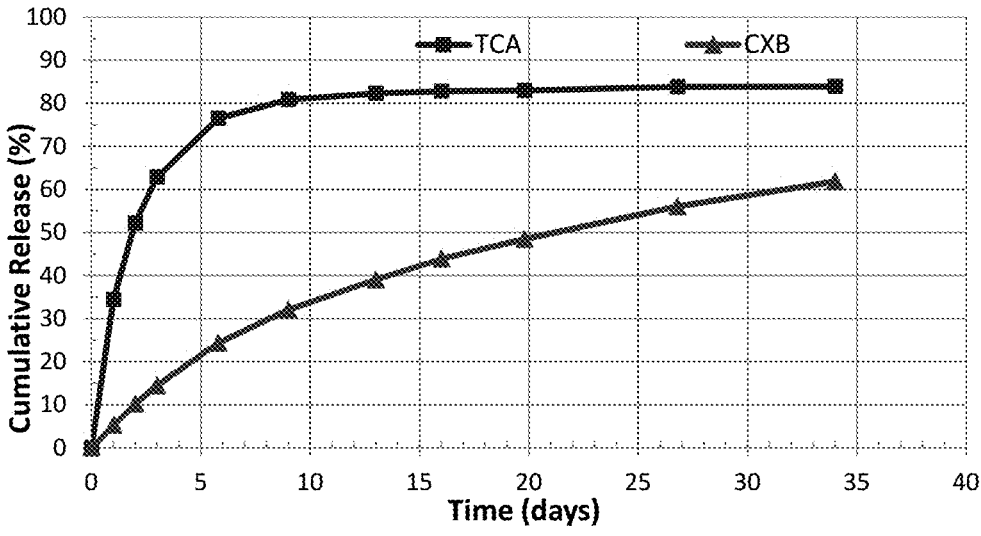
FIG. 5 illustrates the in vitro release profile of triamcinolone acetonide and celecoxib of Formulation #5 in PBS Buffer w/0.5% SDS, pH 7.4, Shaking Water Bath, 37° C. given in Example 3.

In both Formulation #3 and #4, a medium-to-high molecular weight, ester end-capped PLGA with L/G ratio of 50:50 (Resmer® RG505) was used. With dichloromethane as the dispersed organic phase solvent, Formulation #3 gives a very fast initial release of TCA and a slower release of CXB (FIG. 3), while when using a mixture of dichloromethane and ethyl acetate (1:1) as the organic phase solvent, the release rate of both drugs slow down (FIG. 4).

Figure 6:
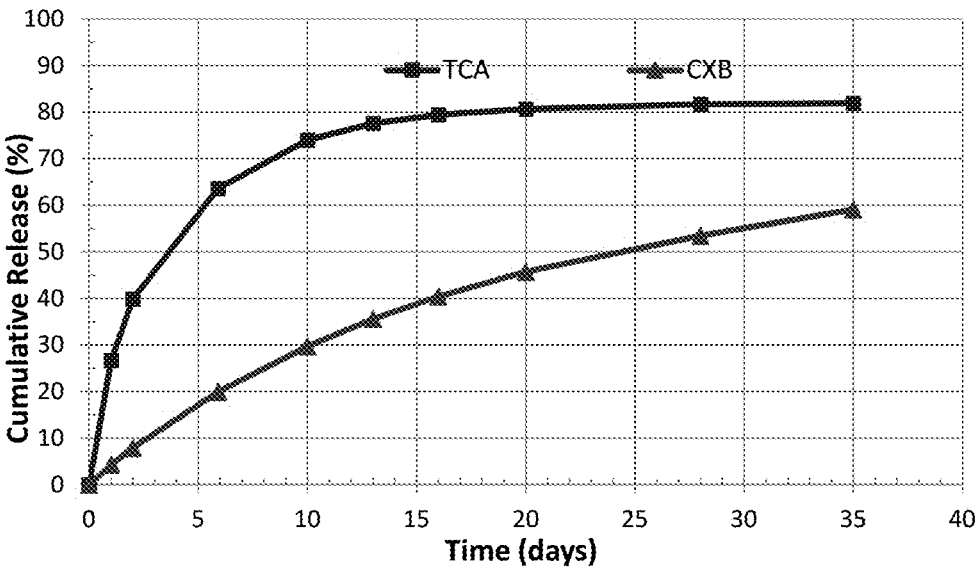
FIG. 6 illustrates the in vitro release profile of triamcinolone acetonide and celecoxib of Formulation #6 in PBS Buffer w/0.5% SDS, pH 7.4, Shaking Water Bath, 37° C. given in Example 3.
Figure 7:
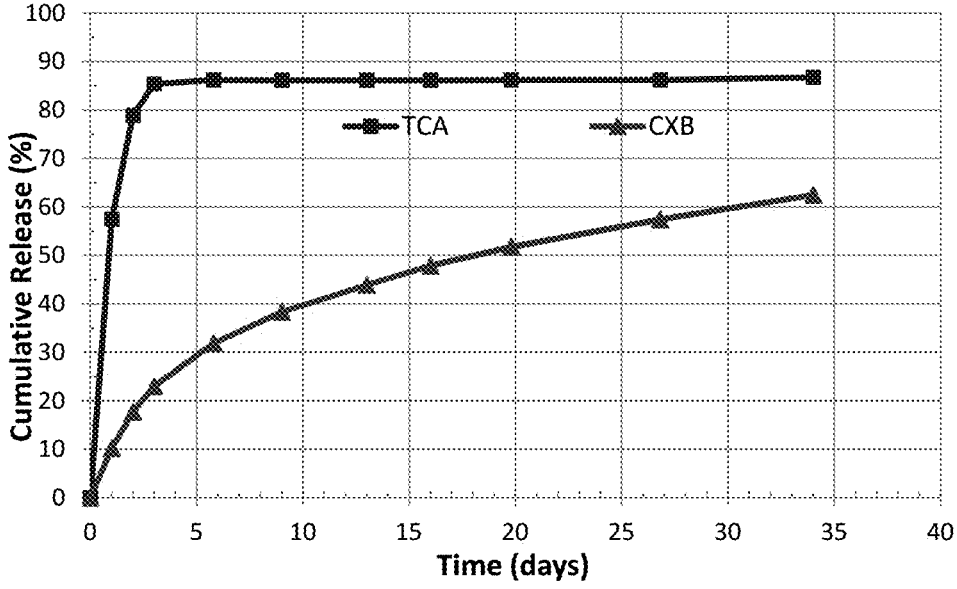
FIG. 7 illustrates the in vitro release profile of triamcinolone acetonide and celecoxib of Formulation #7 in PBS Buffer w/0.5% SDS, pH 7.4, Shaking Water Bath, 37° C. given in Example 3.

In both Formulation #5 and #6, a medium-to-high molecular weight, carboxyl end-capped PLGA with L/G ratio of 75:25 was used. With dichloromethane as the dispersed organic phase solvent, Formulation #5 gives a fast initial release of TCA and a much slower release of CXB (FIG. 5), while when using a mixture of dichloromethane and ethyl acetate (1:1) as the organic phase solvent, the initial release rate of TCA slows down (FIG. 6).

In Formulation #7, a medium-to-high molecular weight, ester end-capped PLGA with L/G ratio of 75:25 was used. In the in vitro cumulative release profile, TCA was almost completely released within the first 3 to 4 days, while the CXB was released in a sustained mode for a long time.

Figure 8:
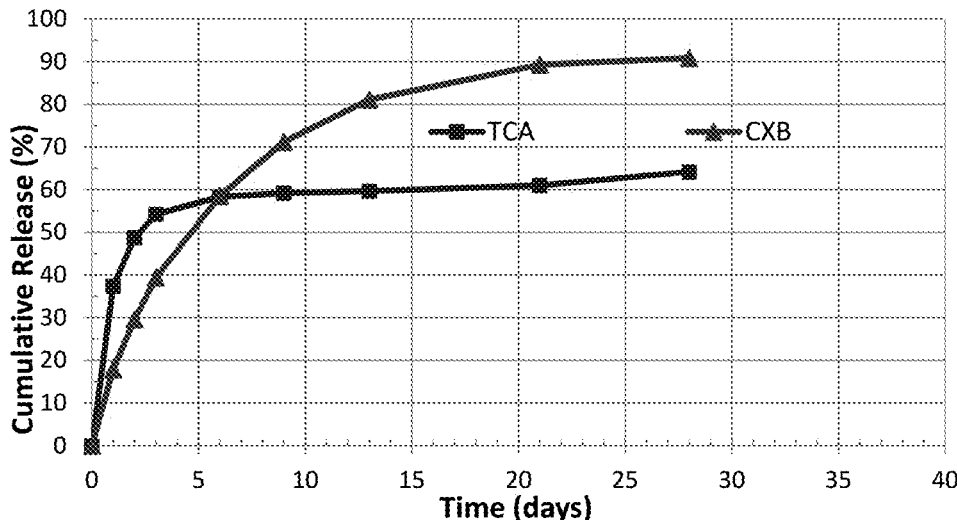
FIG. 8 illustrates the in vitro release profile of triamcinolone acetonide and celecoxib of Formulation #8 in PBS Buffer w/0.5% SDS, pH 7.4, Shaking Water Bath, 37° C. given in Example 3.

In Formulation #8, a mixture of a low molecular weight, carboxyl end-capped PLGA and a medium-to-high molecular weight, ester end-capped PLGA, both with L/G ratio of 50:50, was used. In the in vitro cumulative release profile, CXB was initially released faster than TCA within the first few days, and slows down later (FIG. 8).

Example 4: HPLC Method for Determination of the Drug Loading Percentages in Microsphere Formulations Chromatographic Parameters:

Column: Phenomenex Luna C18(2), 5 µm, 4.6 mm×250 mm

Column temperature: 40° C.

Mobile phase: acetonitrile/methanol/water 53:15.7:31.3 (v/v/v)

Flow rate: 1.0 mL/min

Injection volume: 20 µL

Detector: UV at 245 nm

The standard solution was prepared by weighing approximately 30 mg of API reference standard into a 100-mL volumetric flask, adding approximately 80 mL of methanol, mixing and sonicating to dissolve, and making up to volume with methanol. The stock standard solution was further diluted 1/10 with methanol/water (3:1) to make a working standard of approximately 30 µg/mL of each API.

A sample solution was prepared by weighing approximately 20 mg of drug-loaded PLGA microspheres into a 100-mL volumetric flask, adding approximately 30 mL of acetonitrile, mixing and sonicating to dissolve the microspheres, and then adding 60 mL of water, and finally adding methanol to the volume. The sample solution was filtered through 0.45 µm PVDF syringe filter before the HPLC injection. The percent of drug loading is calculated by:

Drug Loading (%)=Weight of API in Microsphere Sample/Total Weight of Microspheres

Example 5: In Vitro Release Testing of Drug-loaded Microsphere Formulations and HPLC Method for Analyzing Drug Substances in In Vitro Release Samples The in vitro release testing of the drug-loaded microspheres was achieved by suspending approximately 10 mg of the microsphere sample in 21 mL of release medium. The release medium comprised the PBS buffer added with 0.5% of SDS and 0.02% sodium azide, and the pH was adjusted to about 7.40. The sample suspension was contained in a 60-mL cylindrical glass jar (closed with cap), which was placed in a 37° C. water bath shaking at a speed of 90 RPM. At each predetermined sampling time point, 20 mL of the medium was drawn through a 5-μm stainless steel mesh filter, and 20 mL of fresh medium was added back to resuspend the microsphere particles. The sample solution was filtered through a 0.45 μm PVDF syringe filter before the HPLC injection.

The chromatographic parameters used are the same as in Example 4.

Cumulative percentage of drug release is calculated based on the amount of drug released into the total medium divided by total amount of drug in initial microspheres.

Example 6: Particle Size Distribution of Microsphere Samples

Figure 9:
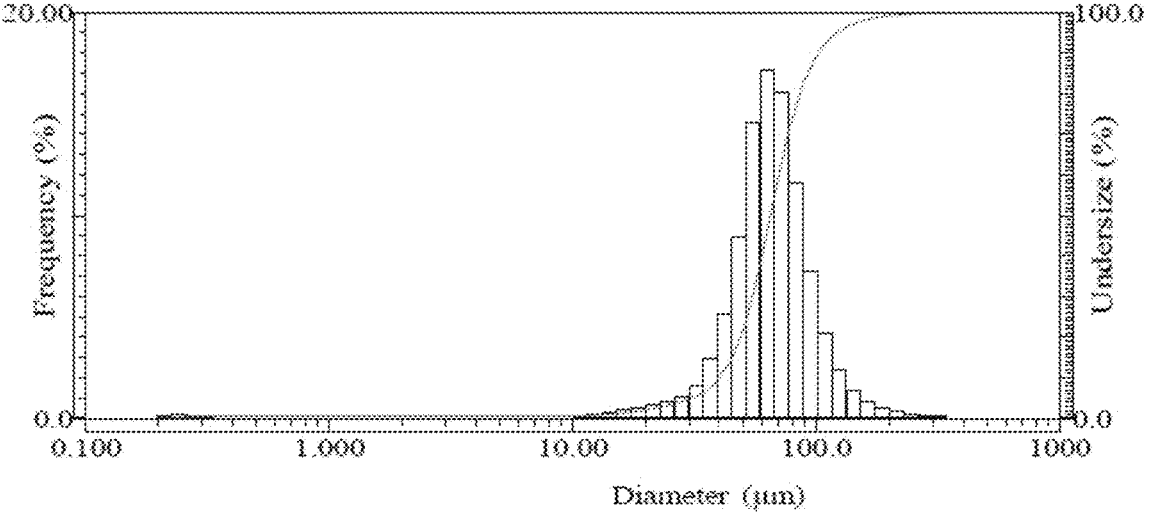
FIG. 9 illustrates the particle size distribution of the microspheres of Formulation #2 provided in Example 2.
Figure 10:
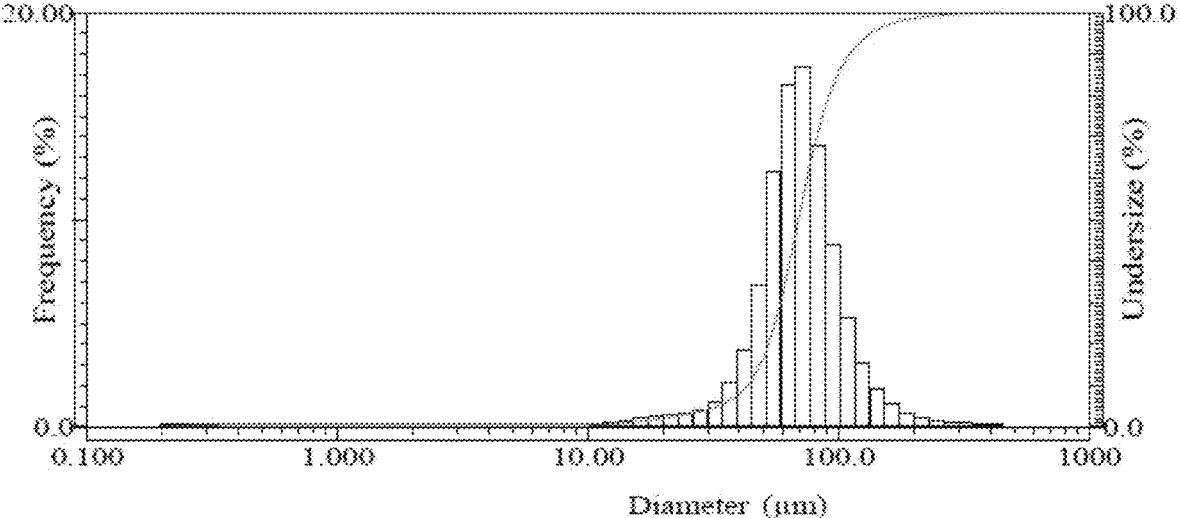
FIG. 10 illustrates the particle size distribution of the microspheres of Formulation #5 provided in Example 3.

The average particle size and size distribution of the microsphere samples were measured with a HORIBA LA-920 laser diffraction particle size analyzer, using DI water as the dispersant and using about 1 mL of 1% PVA to pre-wet the particles. FIG. 9 shows the particle size distribution of MPA/CXB-loaded microsphere preparation of Formulation #2 (in Example 2), and FIG. 10 shows TCA/CXB-loaded microsphere preparation of Formulation #5 (in Example 3). The particle size distribution values (D10, D50, D90, and Span) are given in Tables 2 and 3.

The foregoing examples and description of the certain embodiments should be taken as illustrating, rather than as limiting, the present invention. Numerous variations and combinations of the features set forth above may be used without departing from the present invention.

What is claimed is:

1. An injectable sustained-release formulation, comprising:
   (a) drug microspheres comprising both methylprednisolone acetate (MPA) and celecoxib (CXB) encapsulated in poly(lactic-co-glycolic acid) copolymers (PLGA) with a molecular weight in the range between 10 kD and 130 kD and a molar ratio of lactic acid:glycolic acid between about 50:50 to about 75:25,
   (b) a diluent solution in which the drug microspheres are suspended
   wherein the MPA comprises between 15% and 40% by weight of the drug microspheres and the CXB comprises between 15% to 40% by weight of the drug microspheres;
   the drug microspheres have a mean diameter of between 40 μm and 70 μm; and
   the drug microspheres release at least 30% of the MPA in the first week following parenteral administration to a patient and the remaining MPA is released over at least one month following the parenteral administration to the patient.

2. The formulation of claim 1, wherein the PLGA is a blend of PLGA copolymers having different lactic acid: glycolic acid ratios, and/or different average molecular weights, and/or different chain-end groups.

3. A method of making the injectable sustained-release formulation of claim 1, comprising: (a) preparing the drug microspheres by a solid-in-oil-in-water (S/O/W) emulsion process comprising steps of (i) emulsification, (ii) solvent extraction and evaporation, (iii) particle washing, and (iv) particle drying to obtain the drug microspheres; wherein the emulsification comprises preparing an organic phase liquid by dissolving a PLGA copolymer or a blend of PLGA copolymers and the CXB in an organic solvent, followed by suspending micronized solid particles of the MPA er TCA in the organic phase liquid; and wherein the organic phase liquid is emulsified with a continuous aqueous phase comprising an aqueous solution of polyvinyl alcohol; and (b) suspending the drug-loaded microspheres in a diluent solution.

4. The method of claim 3, wherein the organic solvent is selected from the group consisting of dichloromethane, ethyl acetate, benzyl alcohol, methanol, ethanol, isopropyl alcohol, 1-butanol, iso-butyl alcohol, 1-pentanol, isopentyl alcohol, 1-hexanol, and combinations thereof.

5. The method of claim 4, wherein the organic solvent is a mixture of dichloromethane (DCM) and ethyl acetate (EtOAc).

6. A method of treating arthritis, comprising administering to a subject in need of treatment a therapeutically effective amount of the injectable sustained-release formulation of claim 1.

7. The method of claim 6, wherein the administration comprises locally injecting the formulation into the subject's joint having the arthritis.

8. The method of claim 6, wherein the arthritis is rheumatoid arthritis or osteoarthritis.

9. The formulation of claim 1, wherein the diluent solution comprises hyaluronic acid (HA).

* * * * *